United States Patent
Wellisz et al.

(12) 
(10) Patent No.: US 6,652,531 B2
(45) Date of Patent: *Nov. 25, 2003

(54) BONE ALIGNMENT AND FIXATION DEVICE AND INSTALLATION METHOD, USING ATTACHMENT STRUCTURE

(75) Inventors: Tadeusz Z. Wellisz, Los Angeles, CA (US); Eric V. Hohenstein, Los Angeles, CA (US)

(73) Assignee: Bioplate, Inc., Los Angeles, CA (US)

( * ) Notice: Subject to any disclaimer, the term of this patent is extended or adjusted under 35 U.S.C. 154(b) by 62 days.

This patent is subject to a terminal disclaimer.

(21) Appl. No.: 09/995,444

(22) Filed: Nov. 29, 2001

(65) Prior Publication Data

US 2003/0100901 A1 May 29, 2003

(51) Int. Cl.$^7$ ............................................... A61B 17/56
(52) U.S. Cl. ........................................... 606/72; 606/69
(58) Field of Search ............................ 606/69, 70, 72, 606/75, 86, 104, 151; 29/243.56

(56) References Cited

U.S. PATENT DOCUMENTS

| | | | |
|---|---|---|---|
| 4,936,844 A | | 6/1990 | Chandler et al. |
| 5,674,222 A | | 10/1997 | Berger et al. |
| 5,810,822 A | | 9/1998 | Mortier |
| 5,868,746 A | * | 2/1999 | Sarver et al. |
| 5,953,803 A | * | 9/1999 | Hahn |
| 6,190,389 B1 | * | 2/2001 | Wellisz et al. |
| 6,302,884 B1 | * | 10/2001 | Wellisz et al. |
| 6,511,482 B1 | * | 1/2003 | Wellisz et al. |

* cited by examiner

Primary Examiner—Pedro Philogene
(74) Attorney, Agent, or Firm—Wiliiam W. Haefliger

(57) ABSTRACT

A clip to inter-connect primary and secondary bone zones having edges, comprising in combination a first tab to extend over a surface of the secondary bone zone, above a level defined by that surface; and an extension of the tab projecting below the first level, the extension having a through opening to receive a first projection for penetrating the primary bone zone below the first level.

43 Claims, 5 Drawing Sheets

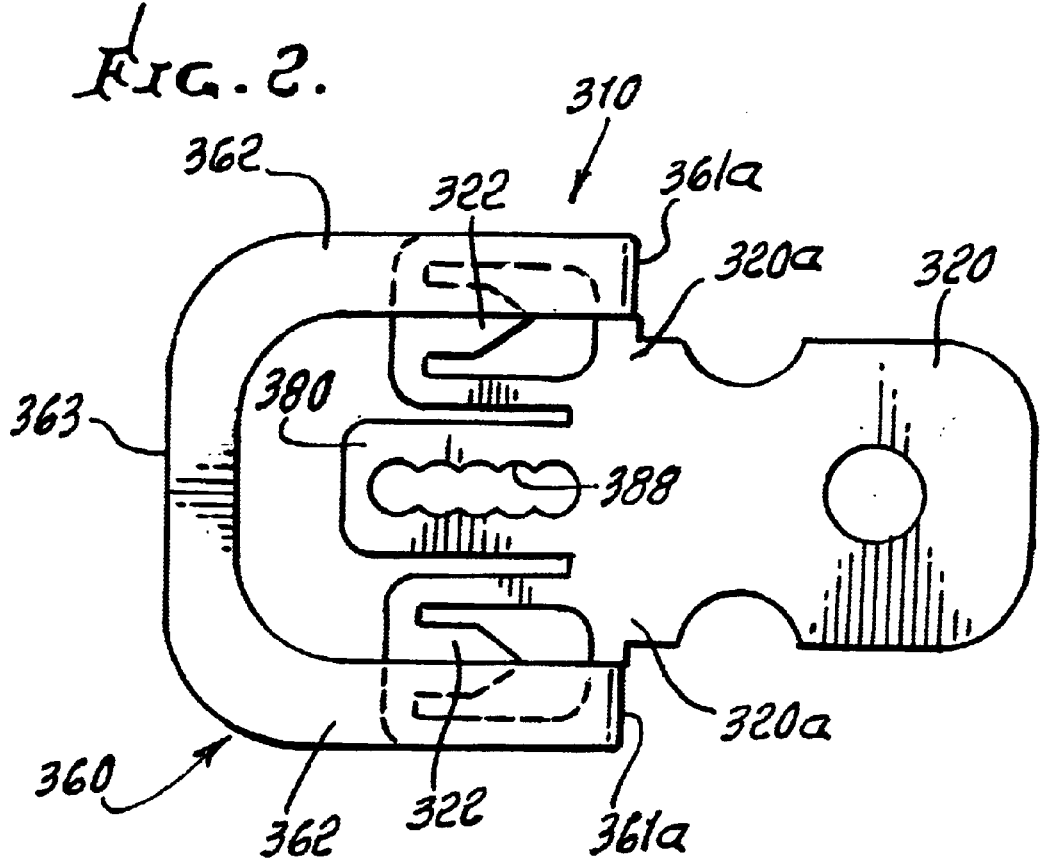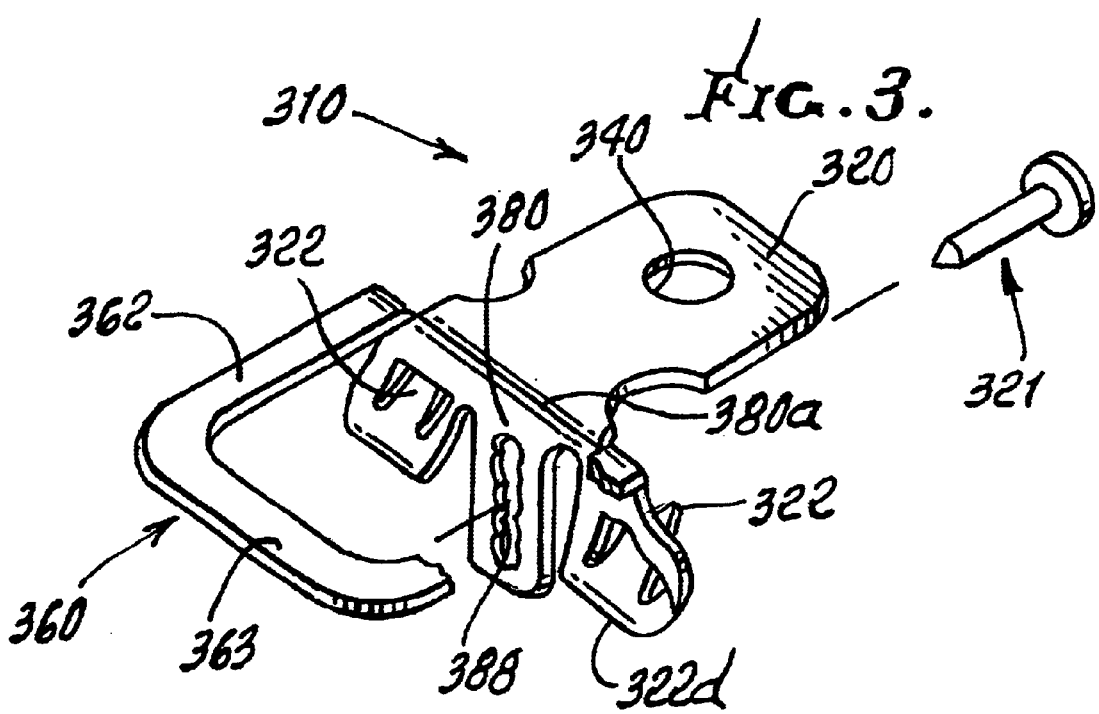

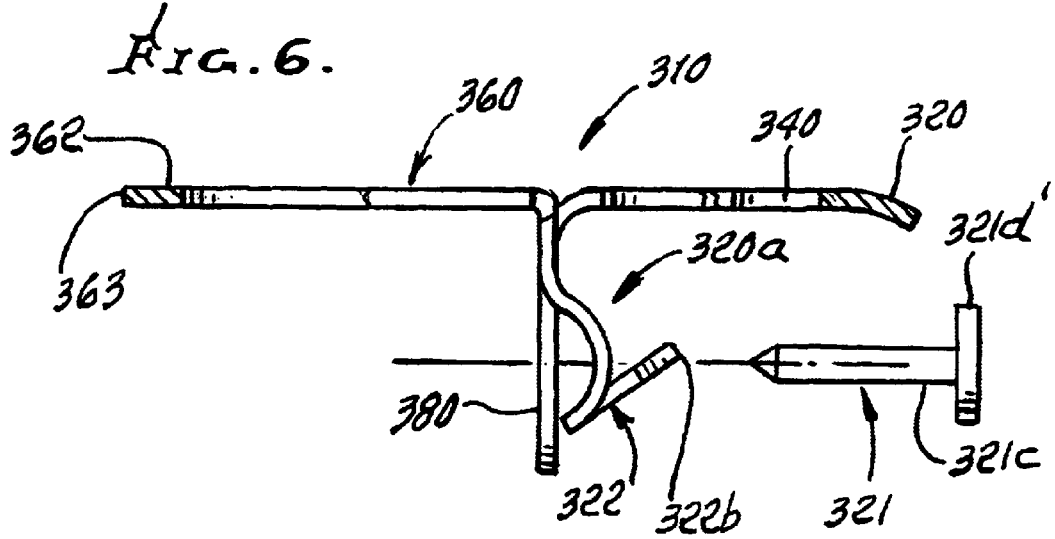
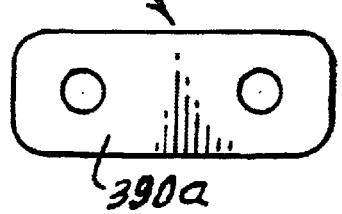
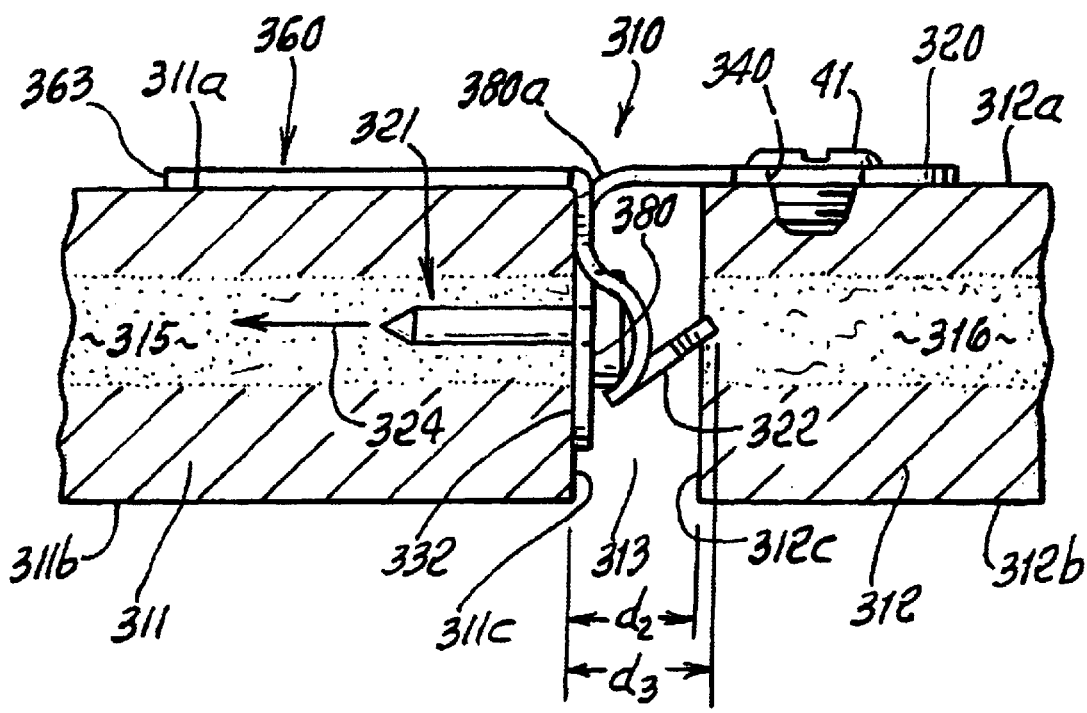

BONE ALIGNMENT AND FIXATION DEVICE AND INSTALLATION METHOD, USING ATTACHMENT STRUCTURE

BACKGROUND OF THE INVENTION

This invention relates generally to the alignment and fixation of bone segments as required for appropriate bone healing, for example after fracture or surgical intervention, and specifically to a device, and the tools needed to install the said device, for the alignment and fixation of cranial bone fragments.

In cases of bone fragmentation where bone fixation is desired, the appropriate alignment of the bone is also a desired result. This is especially true in the cranium, where bone fragmentation can occur as a result of trauma, congenital deformity, or of surgical intervention. In the field of neurosurgery, cranial bone fragments are frequently cut and removed to create defects to allow for access into the cranial cavity and the brain.

The bony cranium is generally regarded to have two surfaces: the outer surface which is characterized by the outer cortex of the bone and is adjacent to the scalp and soft tissue; and the inner surface which is characterized by the inner cortex of the bone and which is adjacent to the cranial cavity and the brain. Between the inner cortex and the outer cortex, which are dense layers of bone, lies the diploe which generally consists of soft bone and bone marrow. When a bone fragment is created, a cut between the bone fragment (the primary bone zone) and the remainder of the cranium (the secondary bone zone) is present.

Several methods of alignment and fixation of primary and secondary bone zones are known. Traditional techniques involve the use of several pieces of filament, such as wire, that are tied after being threaded through holes drilled obliquely through the outer cortex to the cut surface of both bone zones. Precise alignment of the two zones can be difficult and the technique can be cumbersome.

Commonly, the zones of bone can be aligned and fixated with a system of plates and screws (U.S. Pat. Nos. 5,372, 598; 5,413,577; and 5,578,036). A plate made of metal or other substance can be fixated to the outer cortex of the primary bone zone with screws whose penetration of the bone can be limited to the outer cortex. With three or more plates attached to the primary bone in such a way that the plates protrude beyond the edges of the primary bone zone, the primary bone zone can be introduced into a defect and aligned to the outer cortex of the secondary bone zone without danger of the primary bone zone falling too deeply into the defect in the secondary bone zone and exerting pressure on the underlying tissue such as the brain. Fixation can then be achieved by employing additional screws fixating the plates to the outer cortex of the secondary bone zone. Plates and screws systems allow for the alignment and fixation of the zones, while preventing the primary bone zone from falling below the level of the secondary bone zone without actually introducing a component of the device below the secondary bone zone. A plate with a spring clip extension has been described (U.S. Pat. No. 5,916,217). Plate and screw systems can be expensive and time consuming to use.

Devices that align the two bone zones by way of compressing them between the two disks positioned along the inner and outer cortex have been described. (Foreign Patents: DE 19603887C2, DE 19634699C1, DE 29812988U1, EP 0787466A1.) A pin connects the two disks aligning and securing two bone zones. These devices introduce foreign material that is left below the inner cortex, and they do not protect the underlying tissue from compression during the installation procedure.

Devices that fixate bone zones using friction forces created by a cam without a component that extends below the inner cortex are known and described (Patent DE 19634697C1). These devices also do not protect the brain from compression during the installation procedure.

Intramedulary pins are well known in the orthopedic fields for alignment of long bones. Such pins have also been described for cranial fixation (U.S. Pat. No. 5,501,685); however, the bone zones can not be aligned in three dimensions with this technique.

There is a need for an alignment and fixation device that is simple and rapid to use, versatile, and ultimately cost effective. There is also need for guidance of and clip attachment, to bone zones.

OBJECTS OF THE INVENTION

One object of the invention is to provide a device and instruments for its use and installation that aligns one cortex of a primary zone with one cortex of a secondary bone zone without extending to the opposing cortex, and which accurately fixates the bone zones to each other. When used in the field of neurosurgery, the device is applied to the primary bone zone and it aligns the outer cortex of the primary bone zone with the outer cortex of the secondary bone zone; it prevents the primary bone zone from entering the cranial cavity; and it provides fixation of the two bone zones. The alignment feature can be used independently from the fixation feature. An example of the use of the alignment feature is in the replacement of a cranial bone fragment which will be held in place by the tissue forces of the scalp, which allows for the bone fragment to be elevated away from the cranial cavity in cases where brain swelling occurs. Fixation can also be applied to attach the alignment device to the bone, using elements alone or in combination such as filaments, screws, rivets, pins, clips, cams, friction or adhesives. The alignment aspect of the invention can also be applied to situations where it is desired to offset the alignment of the bone fragment to the adjacent bone such as where the object is to create a more prominent chin by cutting the bone of the chin and advancing the bone fragment.

One fixation feature of the invention is likewise independent from the alignment feature. The fixation feature of the device relies on the principle that the device is fixated to the primary bone zone and the fixation feature grips the secondary bone zone by means of spring loaded tab or hook elements engaging the soft areas of the medullary space, irregularities along the cut surface, or a slot cut into the cut surface of the secondary bone zone. Another feature is the use of a fastener to be driven into the edge of a primary bone zone to retain the clip in position; and a further feature is the use of an auxiliary foldable tab carried by the clip to aid its positioning.

SUMMARY OF THE INVENTION

The invention provides an improved clip meeting the above need or needs.

As will be seen, the preferred clip is configured to interconnect primary and secondary bone zones having edges spaced apart by a gap, the clip comprising a) a first tab to extend over a surface of the secondary bone zone, above a level defined by that surface, and b) an extension of the tab projecting below said first level, the extension having a through opening to receive a first projection for penetrating the primary bone zone below the first level.

The first projection is typically in the form of a drivable fastener in alignment with that through opening. The opening typically has sections that define a sequence of fastener guide edges, which are discrete to slidably fit the fastener.

As will be seen, a second projection may be provided and carried by the tab and configured to engage the secondary bone zone at the edge thereof, and below said surface level, as well as below the level of the auxiliary tab.

It is another object to provide an extension to carry the second projection, if it is provided. In this regard, the second projection is typically located beneath the first tab; and the first projection is driven generally parallel to that tab and forwardly from a part of the tab extension below said surface level, and it preferably has a sharp terminal to enable penetration of diploe.

A further object is to provide the second projection to have a sharp terminal, and to extend at an angle toward the tab, in order to resist removal relative to the secondary bone zone.

Yet another object is to provide another second projection carried by the tab in sidewardly spaced relation to the first mentioned second projection, and configured to engage the secondary bone zone at the edge thereof, and below said surface level, as well as below the auxiliary tab.

An additional object is to provide a tab extension as referred to, but having S-shape or configuration, whereby enhanced spring support of one or both projections is realized; and also the S-shape of the extension facilitates its formation or manufacture.

Another object is to provide an auxiliary tab associated with the first tab to be positioned to extend over a top surface of the primary bone zone to assist positioning of the clip as the first projection penetrates the primary bone zone.

An additional object is to provide a plate or flap defining the primary bone zone, and to provide multiple of the clips having their first projections penetrating the primary bone zone at different edges thereof, below a surface defined by the plate or flap.

The method of using the clip as referred to includes orienting the clip first projection to align with said through opening, and driving the first projection via that through opening into the primary bone zone at the edge thereof.

As will be seen, the first projection such as a fastener is preferably carried to penetrate through a selected section of the through opening and into the primary bone zone. The method may further include providing a second projection carried by the tab and configured to engage the secondary bone zone at the edge thereof, and below its top surface level, the method including displacing the clip and said second projection to engage the secondary bone zone at the edge thereof, below said surface level. An additional step includes displacing the clip in a direction to effect scraping of the edge of the secondary bone zone by the second projection, the second projection oriented to resist reverse displacement of the clip in an upward or opposite direction relative to the secondary bone zone. In this regard, the method may include effecting penetration of the edge of the secondary bone zone by the second projection in an angular direction toward the tab. The bowed or S-shape of the extension, if provided, has enhanced spring effect to aid in effecting such penetration.

The method may include providing an auxiliary tab associated with the first tab to be positioned to extend over a top surface of the primary bone zone to assist positioning of the clip as the first projection penetrates the primary bone zone. The method may include bending the auxiliary tab away from said first tab, and into a position of clip stabilizing engagement with the top surface of the primary bone zone.

These and other objects and advantages of the invention, as well as the details of an illustrative embodiment, will be more fully understood from the following specification and drawings, in which:

DRAWING DESCRIPTION

FIG. 2 is like FIG. 1, but showing folding of an auxiliary tab;

FIG. 3 is a perspective view of one preferred clip, incorporating the invention;

FIG. 6 is a right side elevation taken on lines 6—6 of FIG. 4;

FIG. 7 is a view like FIG. 6, but showing use of the clip;

FIG. 9 shows a flat strip applicable to the clip of FIG. 6.

DETAILED DESCRIPTION

Figure 8:
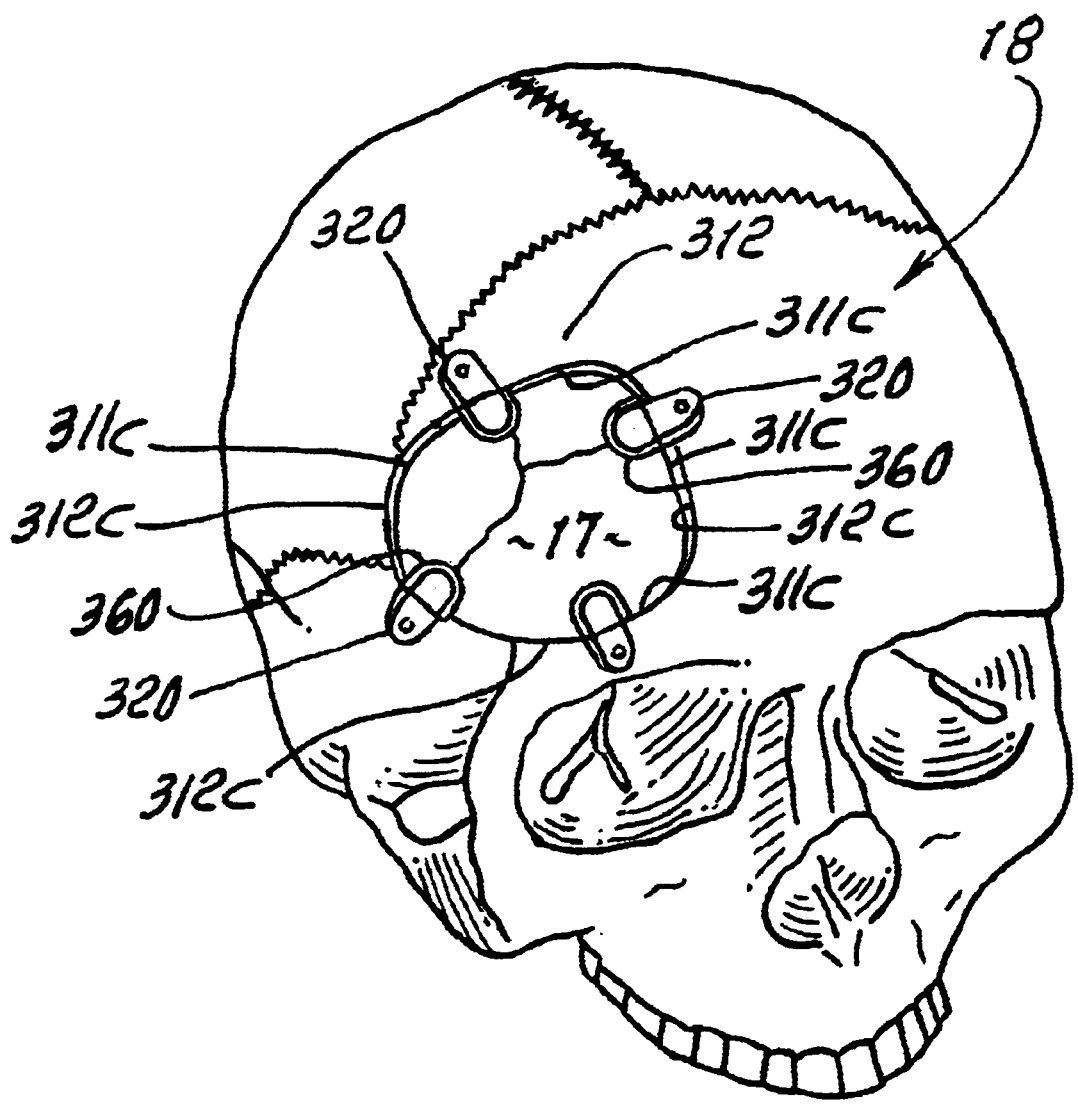
FIG. 8 is a perspective view showing a bone flap fixated on a skull, employing fixation clips.

Referring to FIGS. 3–7, the illustrated and preferred clip 310 is configured to interconnect primary and secondary bone zones 311 and 312 having opposed and spaced apart edges 311c and 312c. A cut or gap 313 is formed between the opposed edges of the primary and secondary bone zones. Diploe is shown at 315 between the top and bottom surfaces 311a and 311b of zone 311; and at 316 between the top and bottom surfaces 312a and 312b of zone 312. As also seen in FIG. 8, primary bone zones 311 may be defined by bone flap 17; and secondary bone zones 312 may be defined by skull 18 and its zone extents at 312 opposing zones 311. In the adult, cranial bone or skull averages 7 mm in thickness, but varies between 3 and 12 mm.

The clip 310, is also shown in blank formed condition in FIGS. 1a, 1b, 1c, and 1d, and in folded condition in FIGS. 2–7. The clip, which is preferably metallic, includes the following:

a) a tab 320 to extend over and generally parallel to a surface 312a of the secondary bone zone 312, above surface level;

b) a first projection or prong 321 configured to penetrate through an opening 388 in the tab downward extension 380, and into the exposed diploe of the primary bone zone 311 at the edge 311c of that zone (and typically into diploe 315).

The clip may include a bendable auxiliary tab, such as tab 360, associated with the first tab 320 to be positioned to extend over a top surface of the primary bone zone to aid in positioning and stabilizing of the clip, such as to guide movement of the clip as the first projection penetrates the primary bone zone.

The clip may include, and preferably does include at least one second projection 322 carried by the tab and configured to engage (for example gouge into) the exposed diploe of the secondary bone zone 312 at its edge 312c, below the level of surface 312a, and below the level of the auxiliary tab 360.

Figure 1A:
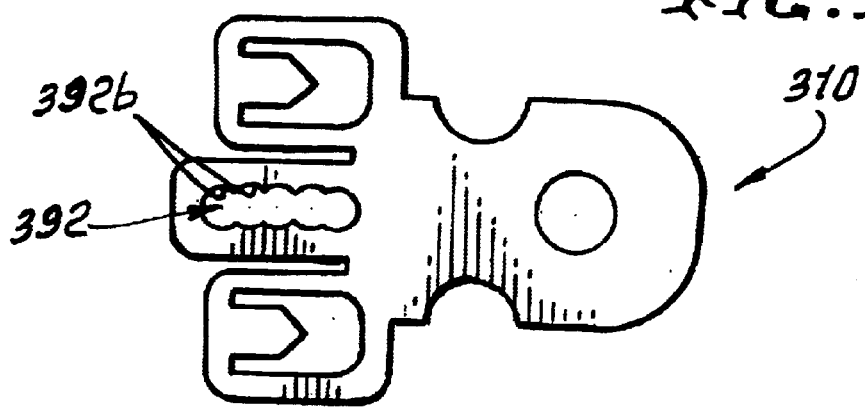
FIG. 1a is a plan view of a clip blank in one plane, prior to deformation.
Figure 1B:
FIG. 1b is a side view of a fastener usable with the FIG. 1a clip.
Figure 1C:
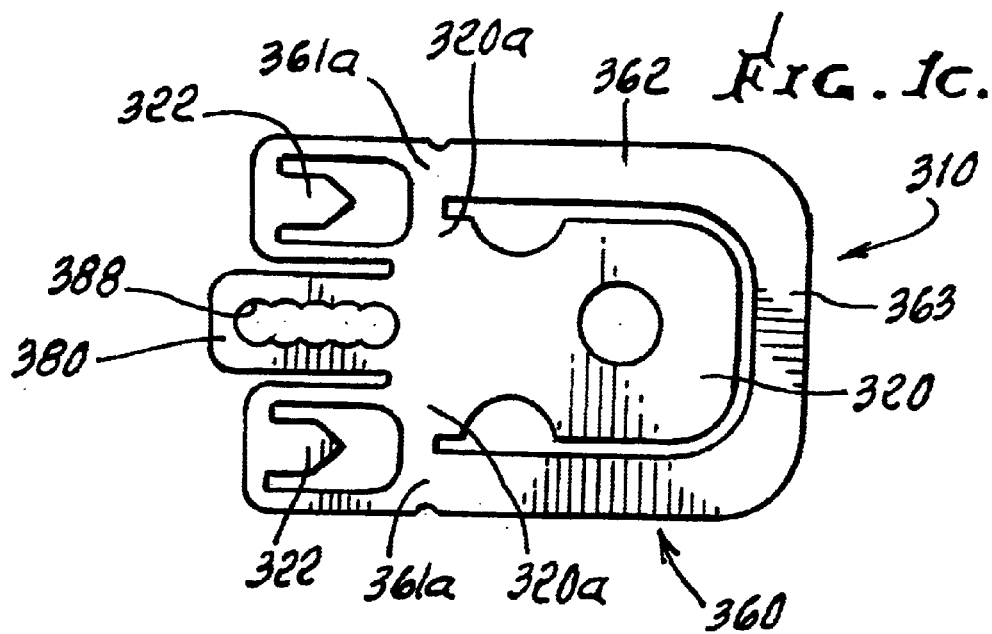
FIG. 1c is a plan view of a modified clip blank, in one plane, prior to deformation.
Figure 1D:
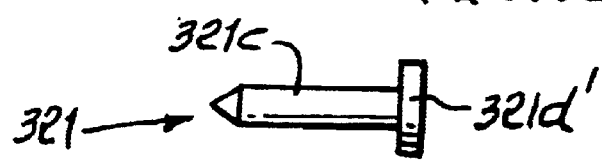
FIG. 1d is a side view of a fastener usable with the FIG. 1c clip.
Figure 4:
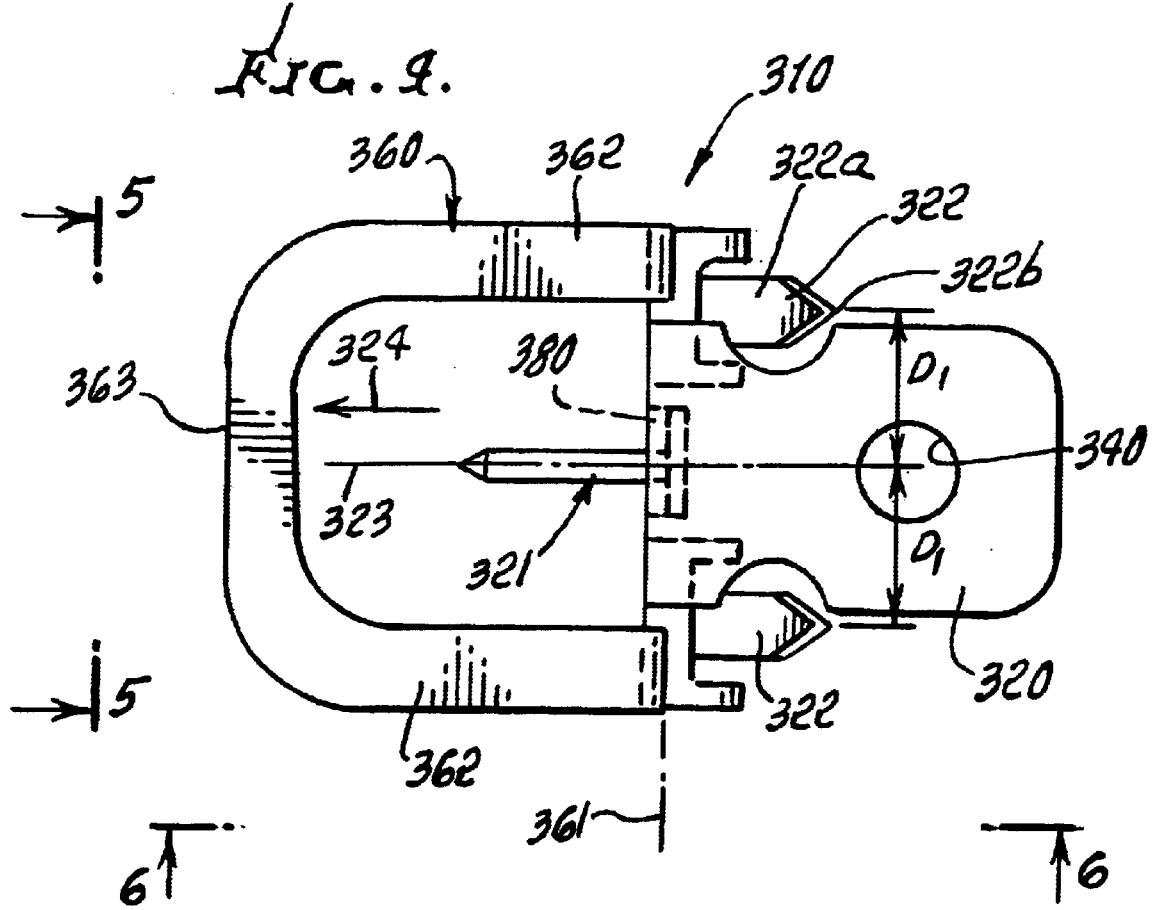
FIG. 4 is a top plan view of the FIG. 3 clip.
Figure 5:
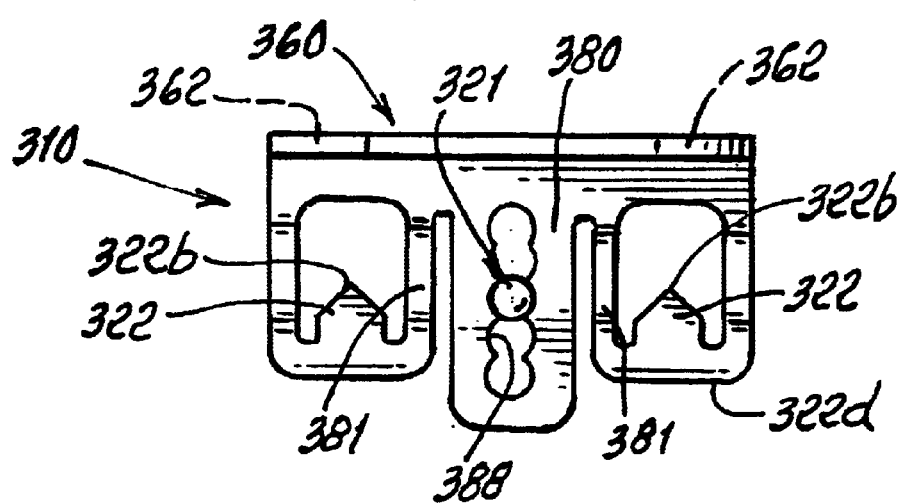
FIG. 5 is a front elevation view of the FIG. 4 clip, and taken on lines 5—5 of FIG. 4.

In the example, two such second projections are provided, as is clear from FIGS. 3–5, and they are located at opposite sides of a lengthwise plane 323 bisecting the clip, including first projection 321. Such projections are equally spaced from plane 323, as indicated by dimensions $D_1$, seen in FIG. 4. The projections 322 have legs 322a, and their terminals are sharpened at 322b, to facilitate penetration of the diploe zones, as seen in FIG. 7. Projection 321 extends forwardly in direction 324 from a tab downward extension 380; and projections 322 extend back upwardly at an angle between 25° and 45° toward the underside of the tab 320. Note that each projection 322 extends from tab ring-shaped extension 320a and is U-shaped. A bend is formed at 322d.

Projection 321 is preferably an elongated fastener having a shank 321c and a head 321d' to be driven forwardly, as by a driver gun; and through an elongated opening 388 in tab downward extension 380. FIG. 1 shows elongated opening 392 as having a sequence of opening sections 392b, for selective positioning of the fastener lengthwise of the opening 392.

It will be noted that the generally upright extension is bowed at 320a to produce an enhanced spring effect for urging one or more of the projections 322, and also to facilitate ease of manufacture. See extension sections 380 and 381, the former bowed frontwardly in the direction of projection 321; and the latter section 381 bowed in the general direction of the projections 322 extents. Section 380 is curved at 380a to merge with the tab. Projection 321 is carried by section 380, and projections 322 are carried by section or sections 381, whereby movements of the projections 322 are isolated from movements of the projection 321, enhancing completeness and permanence of fastening to bone. See for example FIG. 5, showing such isolation.

The method of use of the clip or clips includes orienting the first projection to align with the through opening, and driving the first projection via the through opening into the primary bone zone at the edge thereof. Further steps include:
  i) causing the first projection or projections 321 to penetrate the primary bone zone or zones; as by driving the fastener 321 relative to the extension 380;
  ii) causing the second projection or projections 322 to grip the secondary bone zone at the edge thereof.

As will be seen the method may also include employing an auxiliary tool to guide the clip during such penetration.

Step i) may include pushing the clip 310 relatively toward the edge 311c of the primary bone zone 311, as in direction 324 seen in FIG. 7, while employing the folded auxiliary tab 360 (if used) to engage surfaces 311a and slide forwardly, to effect guiding of push-in penetration of the first projection 321 into the bone zone 11, as for example into diploe 15. See FIG. 7. The auxiliary tab 360 is preliminarily folded forwardly about axis 361, to the position seen in FIGS. 2–3. Push-in is typically completed when bent-down and bowed tab extension 380 closely approaches and/or engages edge 311c of the primary bone zone 311 defined by the plate or flap 17 (or bone zone 311).

As described above, four pushed-in clips are seen in FIG. 8, the clips located in opposed pair positions, at four sides of the flap 17. Each tab 320 has a through hole 340 drilled or formed therein to receive a fastener such as a retention screw, indicated at 41 in FIG. 7, to penetrate and attach to the skull proximate the secondary bone regions. Fastener drive-in is also employed to hold or clamp the extension 380 to edge 311c.

The method preferably also includes displacing the clip in a direction (typically relatively downwardly toward the skull to bring 322, and 320a into gap 313 as seen in FIG. 7) to effect scraping of the edge 312c of the secondary bone zone 312 by the tip or tips of the angled second projection or projections. Projection or projections 322 is or are oriented, i.e. angled, to resist displacement of the clip in an upward or opposite direction, relative to bone zone 12. For example, attempted upward and outward displacement would increase the "gouge-in" movement of the second projection, into the diploe 16.

As described above, the installed spacing $d_2$ of the bone zone edges 11c and 12c is slightly less than the spacing $d_3$ as measured from the sharp terminal of the projection 322 to the surface 332 of the tab extension facing the edge 311c. The width $d_2$ of gap 13 between 311c and 312c is slightly less than the dimension $d_3$, i.e.

$$d_2 < d_3,$$

to provide a desirably tight installation of plate 17 into the corresponding skull opening.

Projections 322 can resiliently deflect, as by spring bending of sections 381, to accommodate the multiple clips to the gaps 13 between 11 and 12, as during plate or tab downward installation. In FIG. 5, the lateral spacing of bowed sections 381 further enhances clip installed stability.

As shown in the drawings, tab 360 is U-shaped, and has two parallel legs 362 joined at their ends 361a to laterally spaced extents 320a of tab 320. Tab 360 has an edge 363 that flatly and slidably engages surface 311a during penetration of projection into diploe 315, to guide and stabilize such penetration.

The clips as referred to above are metallic, and preferably consist essentially of one of the following:
  i) titanium
  ii) titanium alloy
  iii) an alloy consisting essentially of titanium, aluminum and vanadium
  iv) an alloy consisting essentially of:
    about 90% by weight of titanium
    about 6% by weight of aluminum
    about 4% by weight of vanadium.

Further characteristics of the illustrated auxiliary tab 360 include:
  i) it has substantially U-shape and extends about a major portion of the first tab, before it is folded,
  ii) it has a foldable portion proximate an extension of the tab associated with the projection,
  iii) it is connected to the first tab, and comprises a thin plate.

As also seen in FIG. 8 primary bone zones 311 may be defined by bone flap 17; and secondary bone zones 312 may be defined by skull 18 and its zone extents at 312 opposing zones 311. In the adult, cranial bone or skull averages 7 mm in thickness, but varies between 3 and 12 mm.

FIG. 9 shows a flat strip 390 applicable over the tab 320 seen in FIG. 6, to hold it and the clip structure 380 in down position. A portion 390a of strip 390 fits between legs 361 of the auxiliary tab.

A clip installation tool of the type disclosed in FIG. 17 of U.S. Pat. No. 6,190,389 B1 may be used, such disclosure incorporated herein by reference.

We claim:

1. A clip to inter-connect primary and secondary bone zones having edges, comprising in combination:
   a) a first tab to extend over a surface of the secondary bone zone, above a level defined by that surface, and
   b) an extension of the tab projecting below said first level, said extension having a through opening to receive a first projection for penetrating the primary bone zone below said first level.

2. The combination of claim 1 including said first projection in the form of a fastener in alignment with said through opening.

3. The combination of claim 1 including an auxiliary tab associated with the first tab to be positioned to extend over a top surface of the primary bone zone to assist positioning of the clip as the first projection penetrates the primary bone zone.

4. The combination of claim 3 wherein said opening has sections that define a sequence of fastener guide edges which are discrete to slidably fit the fastener.

5. The combination of claim 3 including a second projection carried by the tab and configured to engage the secondary bone zone at the edge thereof, and below said surface level and said auxiliary tab.

6. The combination of claim 5 wherein the second projection is carried by the tab extension.

7. The combination of claim 1 wherein said tab has the form of a plate that extends forwardly and then downwardly to define said extension.

8. The combination of claim 2 wherein said fastener has a sharp terminal to enable penetration of bone marrow.

9. The combination of claim 2 wherein said fastener projects in a direction generally away from said second projection.

10. The combination of claim 6 wherein said second projection has a sharp terminal to enable penetration of diploe.

11. The combination of claim 6 wherein said second projection extends at an acute angle relative to said extension, and toward said tab.

12. The combination of claim 1 including a through hole in the tab to receive a retainer to hold the tab to said surface.

13. The combination of claim 5 including another second projection carried by the tab in sidewardly spaced relation to the first mentioned second projection, and configured to engage the secondary bone zone at the edge thereof, and below said level.

14. The combination of claim 13 wherein each said second projection has a sharp terminal to enable penetration of bone tissue.

15. The combination of claim 12 wherein each second projection extends backwardly at an acute angle toward the tab.

16. The combination of claim 5 including said primary bone zone penetrated by a tip of said first projection, and said secondary bone zone engaged by a tip of said second projection.

17. The combination of claim 1 including a cranial bone flap defining said primary bone zone.

18. The combination of claim 17 including multiple of said clips spaced peripherally about the flap.

19. The combination of claim 5 wherein said second projection is a barb.

20. The combination of claim 19 wherein there are two of said barbs located on zones defined by said tab extension, said zones projecting laterally oppositely relative to said through opening.

21. The combination of claim 1 including attachment wings defined by said extension, and associated with said barbs.

22. The method of using a clip to interconnect primary and secondary bone zones having edges, the clip comprising
   a) a first tab to extend over a surface of the secondary bone zone, above a level defined by that surface, and
   b) an extension of the tab projecting below said first level, said extension having a through opening to receive a first projection for penetrating the primary bone zone below said first level,
   c) said method including orienting the first projection to align with said through opening, and driving the first projection via said through opening into the primary bone zone at the edge thereof.

23. The method of claim 22 including providing said first projection in the form of a fastener in alignment with said through opening.

24. The method of claim 23 wherein said through opening is provided to be elongated to have a sequence of opening sections for selective penetration by said fastener through one of said opening sections.

25. The method of claim 24 wherein said opening sections are provided to define a sequence of fastener guide edges which are discrete and arcuate to slidably fit the fastener.

26. The method of claim 23 wherein said driving includes providing a driving tool, and operating said tool to impact a head defined by the fastener, between said primary and secondary bone zone edges.

27. The method of claim 24 including orienting said sequence of opening sections to extend in a direction generally normal to said surface, and adjacent the edge defined by the primary bone zone.

28. The method of claim 22 including providing an auxiliary tab associated with the first tab to be positioned to extend over a top surface of the primary bone zone to assist positioning of the clip as the first projection penetrates the primary bone zone.

29. The method of claim 28 including bending said auxiliary tab away from said first tab, and into a position to engage the top surface of the primary bone zone.

30. The method of claim 29 including attaching said auxiliary tab to said top surface of the primary bone zone.

31. The method of claim 22 including a second projection carried by the tab and configured to engage the secondary bone zone at the edge thereof, and below said surface level, the method including displacing the clip and said second projection to engage the secondary bone zone at the edge thereof, below said surface level.

32. The method of claim 31 including orienting the second projection at the edge of the secondary bone zone to resist reverse displacement of the clip in an upward or opposite direction relative to the secondary bone zone.

33. The method of claim 32 including effecting penetration of the edge of the secondary bone zone by the second projection in an angular direction toward the tab.

34. A cranial clip comprising, in combination
   a) a clip having a support plate,
   b) a flange integral with the plate and extending away from the plate,
   c) at least one push-in projection protruding from the flange and extending generally parallel to the plate,
   d) said projection having a sharp tip to be advanced into cranial soft bone tissue proximate an edge of the skull,
   e) and a guide on the clip to engage a cranial surface as the sharp tip is advanced into cranial tissue.

35. The clip of claim 34 wherein said guide is bent into position to slidably engage said cranial surface.

36. The combination of claim 34 including an installation tool interfitting the clip for positioning the clip, as the projection advances into said soft bone tissue.

37. The clip of claim 3 wherein said auxiliary tab initially extends about a portion of the first tab.

38. The clip of claim 3 wherein said auxiliary tab has a bendable portion proximate an extension of the tab associated with the through opening.

39. The clip of claim 37 wherein said auxiliary tab has substantially U-shape.

40. The clip of claim 38 wherein said first projection is received by an extension of the first tab.

41. The clip of claim 3 wherein said auxiliary tab is connected to the first tab.

42. The clip of claim 41 wherein said auxiliary tab is a thin plate.

43. The clip of claim 3 including a retention strip fitting over the first tab and extending between legs defined by the auxiliary tab, in a folded position thereof.

* * * * *